United States Patent [19]
Wilk

[11] Patent Number: 5,247,940
[45] Date of Patent: Sep. 28, 1993

[54] METHOD FOR DETECTING PHLEBITIS

[76] Inventor: Peter J. Wilk, 185 W. End Ave., New York, N.Y. 10023

[21] Appl. No.: 964,208

[22] Filed: Oct. 20, 1992

[51] Int. Cl.$^5$ .............................................. A61B 5/00
[52] U.S. Cl. ................................................... 128/736
[58] Field of Search ......................................... 128/736

[56] References Cited

U.S. PATENT DOCUMENTS

| | | | |
|---|---|---|---|
| 3,750,471 | 8/1973 | Bremer | 128/736 |
| 4,633,885 | 1/1987 | Du Brucq et al. | 128/736 |
| 4,665,927 | 5/1987 | Daily | 128/736 |
| 4,813,790 | 3/1989 | Frankel et al. | 128/736 |
| 4,981,139 | 1/1991 | Pfohl | 128/736 |
| 5,017,019 | 5/1991 | Pompei | 128/736 |
| 5,060,657 | 10/1991 | Teague | 128/736 |

Primary Examiner—Max Hindenburg
Attorney, Agent, or Firm—R. Neil Sudol; Henry D. Coleman

[57] ABSTRACT

A device for detecting phlebitis comprises a housing and a plurality of temperature sensors mounted to the housing in spaced relation to one another so that the sensors are disposable in juxtaposition with a skin surface. A comparator mounted to the housing is operatively connected to the sensors for comparing temperatures simultaneously detected by the sensors upon juxtaposition thereof with the skin surface. The comparator includes a circuit or other component for generating a signal upon the detecting by the comparator of a temperature difference greater than a predetermined threshold. An indicator is mounted to the housing and operatively connected to the comparator for providing a sensible indication to an operator in response to the signal.

7 Claims, 1 Drawing Sheet

METHOD FOR DETECTING PHLEBITIS

BACKGROUND OF THE INVENTION

This invention relates to a device for use in the detection of phlebitis. This invention also relates to an associated method for detecting phlebitis.

Phlebitis is a serious problem in hospitals. Many patients on intravenous lines contract phlebitis. Occasionally fatalities result.

A need exists for a technique which will result in the early detection of phlebitis, before the condition becomes severe.

OBJECTS OF THE INVENTION

An object of the present invention is to provide a method which will result in the early detection of phlebitis, before the condition becomes severe.

Another object of the present invention is to provide an associated device for use in the monitoring of patients with intravenous feed lines, to determine instances of incipient phlebitis.

Another, more particular, object of the present invention is to provide such a device which is easy to use.

These and other objects of the present invention will be apparent from the drawings and detailed descriptions herein.

SUMMARY OF THE INVENTION

A device for detecting phlebitis comprises, in accordance with the present invention, a housing and a plurality of temperature sensors mounted to the housing in spaced relation to one another so that the sensors are disposable in juxtaposition with a skin surface. A comparator mounted to the housing is operatively connected to the sensors for comparing temperatures simultaneously detected by the sensors upon juxtaposition thereof with the skin surface. The comparator includes a circuit or other component for generating a signal upon the detecting by the comparator of a temperature difference greater than a predetermined threshold. An indicator is mounted to the housing and operatively connected to the comparator for providing a sensible indication to an operator in response to the signal.

According to another feature of the present invention, the sensors are greater in number than three and are disposed in a substantially planar array. For example, the sensors may be disposed in a triangular or cross-shaped array. Preferably, the sensors are infrared sensors.

According to a further feature of the present invention, the indicator provides a visual and/or auditory alert signal.

A method for use in detecting phlebitis comprises, in accordance with the present invention, the steps of (a) automatically sensing temperature at a plurality of spaced points on a skin surface simultaneously, (b) automatically comparing temperatures sensed at the spaced points, (c) automatically generating a signal upon detecting a temperature difference greater than a predetermined threshold, and (d) automatically providing a sensible indication to an operator in response to the signal.

Pursuant to another feature of the present invention, the points of temperature measurement are greater than three and are disposed in a substantially planar array.

Pursuant to an additional feature of the present invention, the step of sensing temperature includes the step of detecting infrared radiation emitted from the points of measurement.

A method and device in accordance with the present invention aids in the early detection of phlebitis. The temperature sensors can be made sufficiently sensitive so that a relatively mild temperature gradient across a skin surface in a region of an intravenous catheter may be immediately detected. Upon detection, the intravenous catheter may be removed and replaced, for example, with a catheter in a different location or even a sterile catheter at the same location. In any event, the site of the original intravenous catheterization may be sterilized with antiseptics and antimicrobial agents.

DETAILED DESCRIPTION

Figure 1:
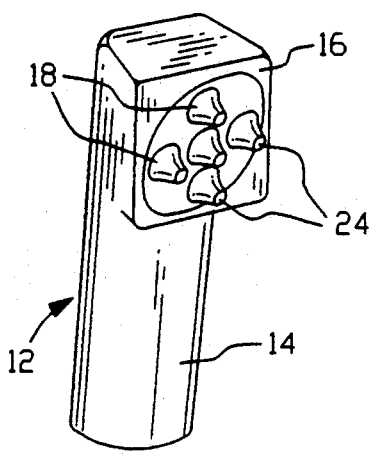
FIG. 1 is a schematic perspective view of a device in accordance with the present invention for use in detecting phlebitis.
Figure 2:
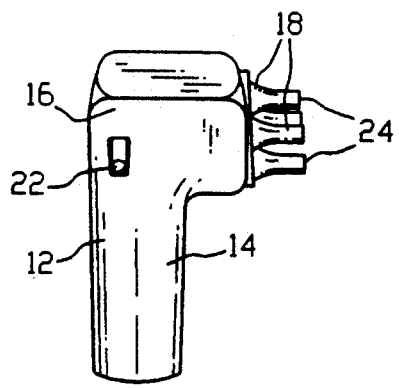
FIG. 2 is a side elevational view of the device of FIG. 1.

As illustrated in FIGS. 1 and 2, a device for use in detecting phlebitis comprises a housing or casing 12 with a handle portion 14 and a head portion 16. Mounted to head portion 16 are a plurality of finger-like extensions or caps 18 which contain respective infrared temperature sensors 20 (FIG. 3) in a cross- or X-shaped array. A switch 22 on head portion 16 provides electrical power to various components (see FIG. 3).

Figure 4:
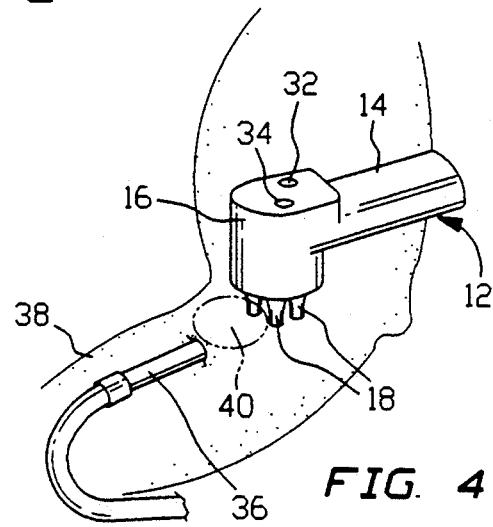
FIG. 4 is a schematic perspective view of a device similar to that of FIGS. 1-3, showing use of the device in monitoring temperature of skin surface in a region about an intravenous catheter.

Sensors 20 are camera-like eyes that measure infrared heat radiating from a skin surface with which free ends 24 of caps 18 are in contact during a temperature sensing operation as depicted in FIG. 4. Sensors 20 are similar to those found in a commercially available device sold under the trademark THERMOSCAN™, for measuring the temperature of the eardrum.

Figure 3:
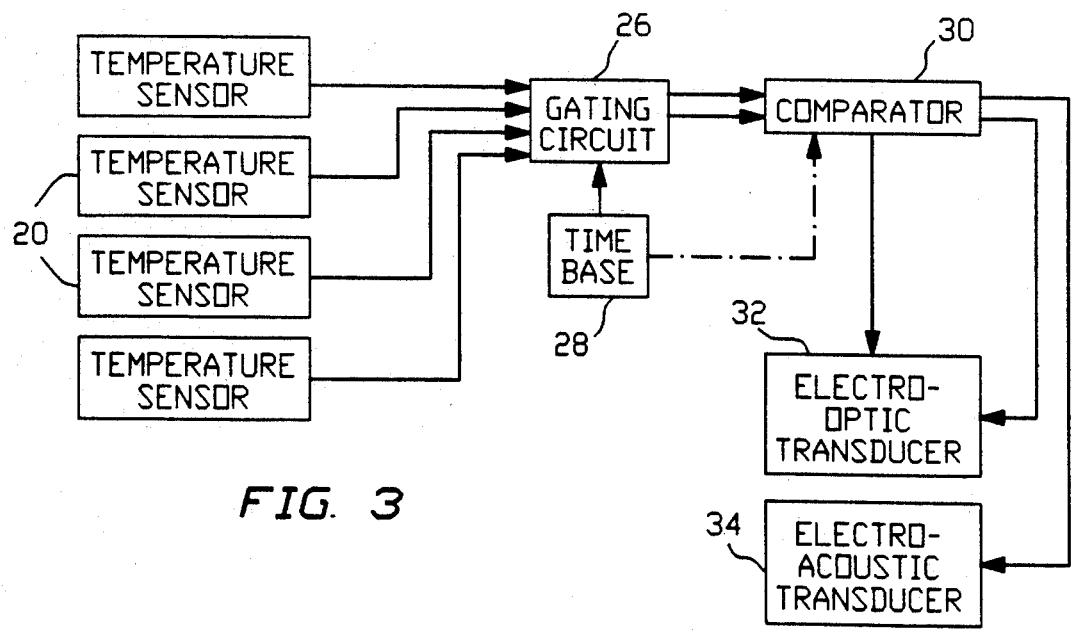
FIG. 3 is a block diagram of functional components of the device of FIGS. 1 and 2.

As further illustrated in FIG. 3, temperature sensors 20 are connected at their outputs to a gating circuit 26 which selects, in accordance with clock signals from a time base 28, pairs of incoming temperature-encoding signals for transmission to a comparator 30. Comparator 30 thus monitors the differences in the temperatures measured by the different pairs of sensors 20 selected by gating circuit 26. Upon detecting a temperature difference greater that a preselected maximum, comparator 30 issues an alert signal to an electro-optical transducer 32 and/or an electro-acoustic transducer 34. Transducers 32 and 34 generate visually and aurally detectible indications, respectively, to alert a human operator to the presence of a temperature differential or gradient possibly indicative of incipient phlebitis.

FIG. 4 depicts a step in a procedure for measuring temperature gradients in the region of an intravenous catheter 36 inserted into a patient's arm 38. Casing 12 is manipulated to place free ends 24 of sensor caps 18 into close juxtaposition or contact with a skin surface 40 over an inserted portion of catheter 36. This position is maintained for a period long enough to allow sensors 20 to equilibrate.

Although the invention has been described in terms of particular embodiments and applications, one of ordinary skill in the art, in light of this teaching, can generate additional embodiments and modifications without departing from the spirit of or exceeding the scope of the claimed invention. Sensors 20 or caps 18 may assume an alternative configuration or array such as a plurality of concentric circles, a triangle with a center sensor, etc. Moreover, the circuitry illustrated in FIG. 3 for monitoring temperature gradients or differentials may assume other, equivalent forms. For example, a plurality of comparators may be provided for monitoring measured temperature differences corresponding to respective fixed pairs of temperatures sensors. Alternatively, a logic circuit or microprocessor may be provided for analyzing several measured temperatures simultanneously. In that event, the microprocessor may calcuate an average measured temperature and compare that average with a temperature difference threshold.

Accordingly, it is to be understood that the drawings and descriptions herein are profferred by way of example to facilitate comprehension of the invention and should not be construed to limit the scope thereof.

What is claimed is:

1. A method for caring for a patient, comprising the steps of:
   automatically sensing temperature at a plurality of spaced points on a skin surface of a patent simultaneously, said points being located generally over an inserted portion of an intravenous catheter traversing said skin surface;
   automatically comparing temperatures sensed at said spaced points;
   automatically generating a signal upon detecting a temperature difference greater than a predetermined threshold;
   automatically providing a sensible indication to an operator in response to said signal; and
   in response to said sensible indication, removing said intravenous catheter from the patient.

2. The method defined in claim 1 wherein said points are greater in number than three and are disposed in a substantially planar array.

3. The method defined in claim 1 wherein said step of sensing temperature includes the step of detecting infrared radiation from said points.

4. The method defined in claim 1 wherein said indication is a visual alert signal.

5. The method defined in claim 1 wherein said indication is an audible alert signal.

6. The method defined in claim 1, further comprising the step of sterilizing said skin surface at and about a point of insertion of said catheter into the patient, said step of sterilizing being executed subsequently to said step of removing.

7. The method defined in claim 1, further comprising the step of introducing a new catheter into the patient in response to said sensible indication.

* * * * *